United States Patent [19]

Obersat

[11] Patent Number: 5,266,032

[45] Date of Patent: Nov. 30, 1993

[54] DENTAL CROWN AND RIGID CONNECTOR

[76] Inventor: Adam Obersat, Logenstrasse 4, 6750 Kaiserslautern, Pfalz, Bundesrepublik, Fed. Rep. of Germany

[21] Appl. No.: 839,251

[22] Filed: Feb. 20, 1992

[30] Foreign Application Priority Data

Feb. 22, 1991 [DE] Fed. Rep. of Germany ... 9102106[U]

[51] Int. Cl.$^5$ .............................................. A61C 5/08
[52] U.S. Cl. ..................... 433/218; 433/219
[58] Field of Search ............... 433/218, 219, 220, 221

[56] References Cited

U.S. PATENT DOCUMENTS

| 376,603 | 1/1888 | Low | 433/221 |
|---|---|---|---|
| 731,594 | 6/1903 | Mosley | 433/220 |
| 977,558 | 12/1910 | Schweitzer | 433/220 |
| 984,782 | 2/1911 | Starr | 433/220 |
| 4,332,564 | 6/1982 | Lord | 433/218 |
| 4,627,136 | 12/1986 | Kreylos et al. | 29/160.6 |
| 4,795,345 | 1/1989 | Ai et al. | 433/202.1 |
| 4,828,496 | 5/1989 | Lococo | 433/224 |

FOREIGN PATENT DOCUMENTS

0136671 9/1984 European Pat. Off. .

*Primary Examiner*—Gene Mancene
*Assistant Examiner*—Cindy A. Cherichetti
*Attorney, Agent, or Firm*—Ostrolenk, Faber, Gerb & Soffen

[57] ABSTRACT

The invention concerns a dental crown, with a facing for example on the visible side for example, and a rigid connector for receiving the crown. The respective co-operating walls telescope for securing the removable prosthesis. The crown is secured to a stump left in the jaw. It has a lingual functional surface with a supragingival cervical offset, a supporting surface adjacent to the prosthesis saddle, and an intracoronal channel extending across the crown more or less parallel to the lingual functional surface. The rigid connector has three friction cylinders, a lingual outer wall which is between the first and second friction cylinder, a supporting telescope wall with the saddle for the prosthesis secured to it, and a patrix web which is inserted in the intracoronal channel. The outer telescope wall, supporting telescope wall, and patrix web of the connector completely surround a web on the crown. The satisfactory hold between the components of the prosthesis derives primarily from friction between their facing parallel walls, for which the friction cylinders and closed-telescope structure are primarily responsible.

26 Claims, 5 Drawing Sheets

DENTAL CROWN AND RIGID CONNECTOR

BACKGROUND OF THE INVENTION

The present invention relates to a dental crown and to a rigid connector for the crown to secure to a removable prosthetic tooth telescopingly in place, the securement occurring through parallel walls of the crown and the connector engaging functionally. The invention also concerns the rigid connector itself and concerns a ceramic core useful for precisely manufacturing such a crown.

Missing teeth can be replaced in the mouth by either a permanent or a removable prosthesis. The present invention addresses the removable type.

Missing teeth are replaced with removable structures. A partial prosthesis is secured to the remaining natural teeth so as to distribute the force of the bite between them and the tegument. A partial prosthesis comprises three elements, namely artificial teeth, a base, and structural elements. The structural elements constitute cushioning elements and connectors. The connectors are either fasteners, resilient connectors, pivoting connectors, or rigid connectors. The present invention concerns rigid connectors.

A characteristic of rigid connectors is an absence of play between the patrix or the permanent connector installed in the jaw and the matrix on the removable crown placed on the patrix. The matrix and the patrix accordingly combine in every application the functions of support, positioning, and skew prevention. Support is provided by an interior backing, while positioning and skew prevention are provided by ensuring a parallel interface between the matrix and the patrix.

Secure fastening is ensured either by friction between the matrix and the patrix or by additional active or passive fasteners. If the hold depends on friction between the matrix and the patrix, it can be restored when necessary by adjusting their mutual fit. What are called actively activatable connectors are employed. In other cases, either the patrix or the matrix, or both must be replaced to restore a secure hold. In this case, the connectors are called passively activatable.

Rigid connectors are bridges, attachments, and telescopes or double crowns. Rigid connectors in the form of double crowns combine the functions of hold, positioning, skew prevention, and thrust distribution. Holding is ensured in parallel walled telescoping connections by friction between the primary and the secondary components. Since friction is lost from a parallel walled telescoping connection, additional active and passive fasteners are needed, especially in the upper jaw. Appropriate structures include friction pins, bars, spherical springs, and snaps. These additional fasteners are intended to prevent an unstressed prosthesis from coming loose by itself.

Telescoping connections with parallel walls include closed, open, and partial telescoping connections. Telescoping connections with conical walls are called conical crowns and those connections are always closed.

Partial telescoping connections, which may also be called groove-and-shoulder telescoping or groove-shoulder-and-pin telescoping, are employed, particularly to replace front teeth and premolars. The lingual portion of the primary crown or matrix has a groove and shoulder machined into it, and the lingual tooth form is provided by this outer telescoping part or crown. The advantage of a partial telescoping connection is that removing the prosthesis reveals the faced primary telescoping part, and appearance is not affected as it is in the case of full telescoping connections. One drawback of partial telescoping connections is their relatively restricted friction area. They are therefore usually provided with additional friction pins that rest resiliently against the primary crown to augment and prolong the securement. Experience has demonstrated, however, that the additional friction pins break off very rapidly due to material stress and fatigue, when anatomical considerations dictate that they be less than 3 mm long.

All three types of telescoping connections must be made individually by the dental technician. Prefabrication is currently impossible. Since the securement that counteracts the tension and compression accompanying the process of mastication depends only on the friction between the patrix and the matrix, all the cooperating surfaces on the patrix and matrix must be parallel and free of play. Since the connectors are small, the technician must use miniature tools, which undesirably yield resiliently to the resulting pressures.

These drawbacks to the individual manufacture of telescoping connections increase as the heights of the telescoping connections decrease. Partial telescoping connections with parallel walls will no longer function when they are less than approximately 4 mm high.

SUMMARY OF THE INVENTION

It is an object of the present invention to combine the advantages of a full telescoping connection with those of a partial telescoping connection, especially in telescoping connections that are less than 3 mm high.

This object is attained in a dental crown of the type described below in conjunction with a connector as described below.

The present invention starts with a type of crown that is known from partial telescoping connections, especially groove-and-shoulder telescoping connections. A groove and shoulder are machined into the lingual portion of the primary or outer visible crown or matrix, and the lingual tooth form is provided with this outer telescoping part. Even with the prosthesis removed, the concealment of the primary telescoping part remains visible. A web is left in the crown between the additional intracoronal channel and the lingual function surface. That web telescopes down around the rigid connector as the crown is installed, acting to that extent like a full telescoping connection. A web corresponding to the channel simultaneously reinforces the outer telescoping part, which assures more friction over a considerably longer time.

A greater number of friction grooves in the crown, into which matching friction cylinders on the separate connector will fit, helps to increase the friction without interfering with the insertion and extraction of the unstressed prosthesis onto off the installed supporting connector or patrix.

All functional surfaces can in principle have any shape, although it is practical for simplicity for the supporting surface and optionally also the functional surface to be largely flat.

A cervical offset preferably extends in the vicinity of the lingual functional surface, although it can also expand to the vicinity of the supporting surface. The width of the cervical offset should increase as the height of the parallel surfaces between the patrix and the matrix decreases. At a height of approximately 3 mm, the offset can in practical terms disappear, and at a height of 2 mm, it should be about 1 mm wide.

The supporting surface on the crown, which is adjacent to the saddle of the connector or patrix can be at an angle of approximately 20° to 90° to the middle of the maxillary crest. This approach will allow considerable freedom of adaptation to the anatomy of the teeth without sacrificing function.

One preferred embodiment of the invention has a snap-in channel for an active fastener in the supporting surface. An appropriate active fastener of this type is described, for example, in the present inventor's European Application 136 671. Active fasteners prevent the unstressed prosthesis from working loose. To avoid impeding the insertion and extraction of the prosthesis, however, the hold of such fasteners is relatively weak, and they cannot accommodate the compression and tension that accompany the process of mastication.

The present invention also makes it possible to use isolated teeth as posts for supporting prostheses. For this purpose, another supporting surface is provided, which is in addition to the first supporting surface. The other surface may be next to the second prosthesis saddle and faces away from the first support. The lingual functional surface can in this event have a fourth friction groove to increase the effect of the friction with the connector.

The intracoronal channel has particular significance for the present invention. To increase the friction of the telescoping connector even more, it is recommended to provide the channel with at least one angle or bend along its length. It is of advantage for the channel itself to begin and end in the supporting surface. The bottom of the channel is flat in its simplest embodiment. It is, however, also possible for the bottom of the channel to slope down across the tooth from one side to the other, i.e. either toward the tongue or toward the teeth. Yet another friction groove can also be accommodated in the channel wall.

The web of the removable connector or patrix in one preferred embodiment rests against a fulcrum in the form of a ridge in the bottom of the channel in the crown or matrix. The ridge is on the other side of the transverse midline of the tooth from the supporting surface. The ridge is provided because the adhesion between the permanent and removable components of the telescoping connection depends on friction. The ridge does not, however, take full effect until the two connectors tilt in relation to each other subject to the forces that accompany the process of mastication. It has now surprisingly been demonstrated that friction can be considerably improved by shifting the fulcrum for the apparent tilting motion to be beyond the transverse midline of the tooth. The ridge can be provided on the bottom of the web on the removable secondary component that is introduced into the channel instead of on the bottom of the channel itself.

The corresponding releasable connector is also part of the dental crown in accordance with the invention. This connector can be individually created and finished as in a conventional dental prosthesis. Tolerances from the ideal shape, which cannot be ruled out when a device is individually manufactured by hand, will not have to be compensated for due to the specific shape of the crown.

The bottom of the web, which matches the 10 intracoronal channel, is wedge-shaped in one preferred embodiment, and the sharp edge of the wedge faces the tongue. The web in this embodiment is forced by the action of mastication to pivot around its sagittal axis. The sides of the web will accordingly tilt to an especially great extent against the walls of the channel, increasing the friction as desired. Friction can be increased even more by making the lingual side of the web slightly conical.

There can be a transverse bore in at least one friction cylinder in one preferred embodiment of the invention. A friction element of resilient plastic is in that bore. The friction element can have a convex head formed with a friction surface at the front. It has a shaft surrounded by expansion skirts. It also has an optional longitudinal slot. The convex head on this friction element acts like both a spring and a friction-inducing structure. It takes up very little space. If the friction elements are correctly positioned, there will be no metal-to-metal contact when the prosthesis is inserted or extracted. The life of the metal components will be extended. Older prostheses can easily be retrofitted.

Optimal precision, parallelism on the part of all functional surfaces that is, optimal dimensional stability, and optimal strength can be attained when the releasable connector is partly prefabricated on an industrial scale.

Since it is possible only in relatively rare cases for a primary crown to be factory semifinished with the telescopable shape of the invention, it must be possible for the technician to provide a crown that he individually finishes with that shape and to the requisite precision. This can be ensured by employing ceramic cores of the type sometimes used to make T attachments.

It will be evident that the most sensible result will be achieved when the cross-section, possibly also the overall shape, of the core matches that of the releasable component of the connector or that of the cavities in the crown. For this purpose, of course, the dentist must always prepare the stump of the tooth with a specific shape. Since this is not possible in all cases, it will be necessary to adapt the ceramic core to the anatomy of the teeth being handled.

In this connection, it has surprisingly been demonstrated that it is possible to manufacture a core, preferably of a ceramic material, that complies with all of the prerequisites relating to functional surfaces, surface forms, and friction grooves in the form of an extrusion. From a preferably extruded billet of ceramic, the core if formed. Appropriate sections can be trimmed from the billet, it can be subject to baking and can then be ground by the dental technician to meet anatomical requirements.

To facilitate handling, it is recommended that at least one and preferably two cylindrical holders be provided on the outer wall of the core next to the functional surface. The technician can secure the cylinders to a paralleler to maintain the correct position while the primary crown is being modeled.

The ceramic core can advantageously be ground such that the cylindrical holders will project beyond it gingivally and not occlusally. It will therefore become possible to rest the core against an appropriate prepared jaw casting without preventing application of the matching tooth for purposes of verification.

One problem in making prostheses and connectors is that each tooth is different. To adapt to teeth and tooth stumps of various widths, a graduated series of ceramic cores and matching connector components can be employed. Such an approach can be avoided, however, in accordance with one advanced version of the invention wherein there is on the ceramic core between the two cylindrical holders at least one line, along which the core can be separated into two halves. If the core has to be expanded to fit a wider stump, the two halves can be separated apart using an appropriate parallel spreader. The gap between the two halves of the core can then be filled with modeling compound. It is, however, also possible to eliminate the modeling compound and to later remove the metal web occurring at that point during the subsequent metal casting.

An alternative approach uses a wide ceramic core as a point of departure, and enough material is ground out of the middle to adapt the core to a narrow stump with the two halves fitting together with no gap.

Other objects and features of the invention are explained by embodiments of the invention described with reference to the drawings.

DESCRIPTION OF THE PREFERRED EMBODIMENT

Figure 1:
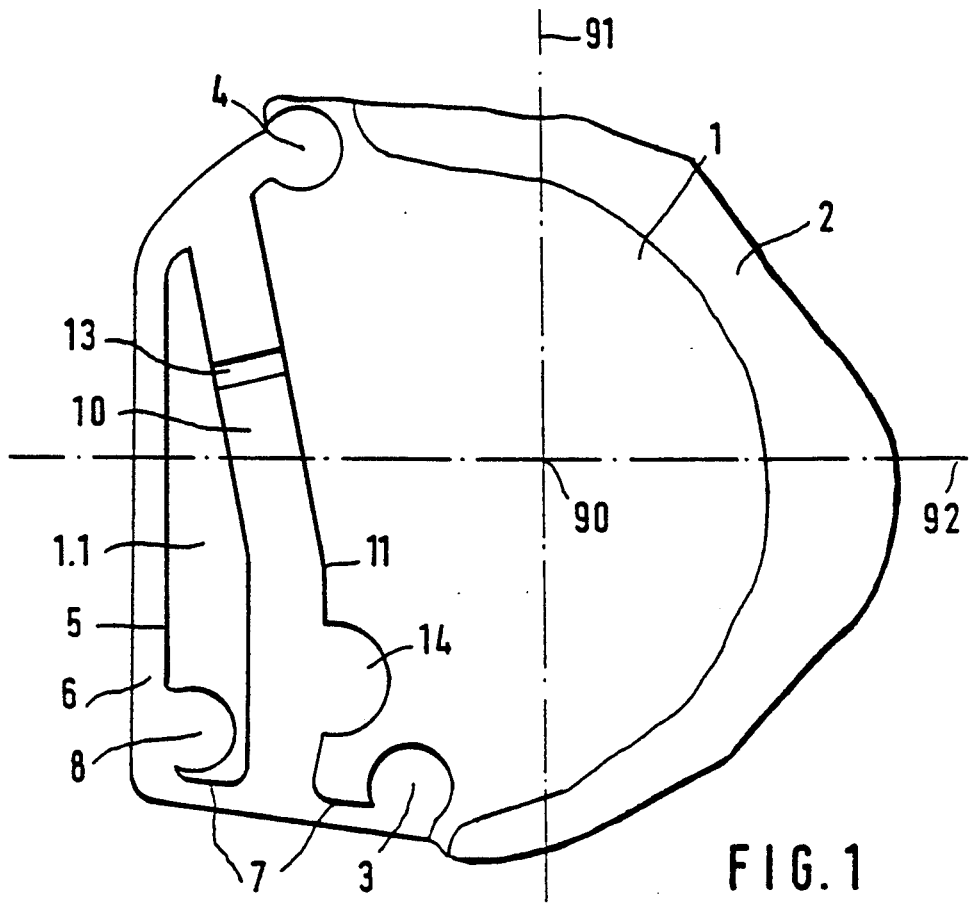
FIG. 1 is an occlusal view of one dental crown or matrix.

FIG. 1 is an occlusal view of one embodiment of a crown 1 according to the present invention. The crown 1 is cast from an alloy of precious metals. Its visible outward side is provided with a facing 2. The center 90 of the tooth, its sagittal midline 91, and its transverse midline 92 are also indicated.

Opposite the outward facing 2 is a lingual functional surface 5, which is flat in the present case and terminates at the bottom in a supragingival cervical offset 6.

The outer surface of the crown 1 accommodates a distolingual friction groove 3 and an opposite side mesiolingual friction groove 4 of the type known from groove-and-shoulder telescoping connections. The lingual functional surface 5 accommodates a third friction groove 8. Friction grooves 3, 4, and 8 are intended to extend the friction interface between the matrix and the patrix and to prevent skewing between those parts.

The friction groove 3 is in the vicinity of a supporting surface 7. For simplicity, that surface is flat and terminates at the bottom in the supragingival offset 6. The supporting surface 7 is primarily intended as a support and to distribute thrust. If there is to be an active fastener, a corresponding depression can be introduced into the supporting surface 7.

A channel 10 extends through the crown 1 from the supporting surface 7. It is essentially parallel to the lingual functional surface 5 which leaves the friction grooves 3 and 4 toward the lingual side of the channel. This leaves a web 1.1 between the lingual functional surface 5 and the channel 10. The web 1.1 is surrounded by the particular patrix 20 employed, which is in the form of a closed and parallel-walled telescoping part. It is accordingly possible to combine the considerable advantages of a full telescoping connection, namely high friction, satisfactory thrust distribution, and long life, with the advantage of a partial telescoping connection, i.e. better appearance with the prosthesis removed.

To increase friction even more, another functional surface 14 in the form of a groove can be introduced in the vicinity of the wall of channel 10. The same purpose is served by an angle or bend 11 in the channel.

In FIG. 1, the bottom wall of the channel 10 can have a ridge 13 on the other side of the transverse midline 92 from the area of the supporting surface 7 which is adjacent to the saddle of the prosthesis. Ridge 13 provides the patrix, which is to be inserted in the crown 1, with a definite fulcrum. This allows optimal surface-to-surface pressure and friction between the matrix and the patrix, subject to the forces on the telescoping connection that accompany the process of mastication.

Figure 2:
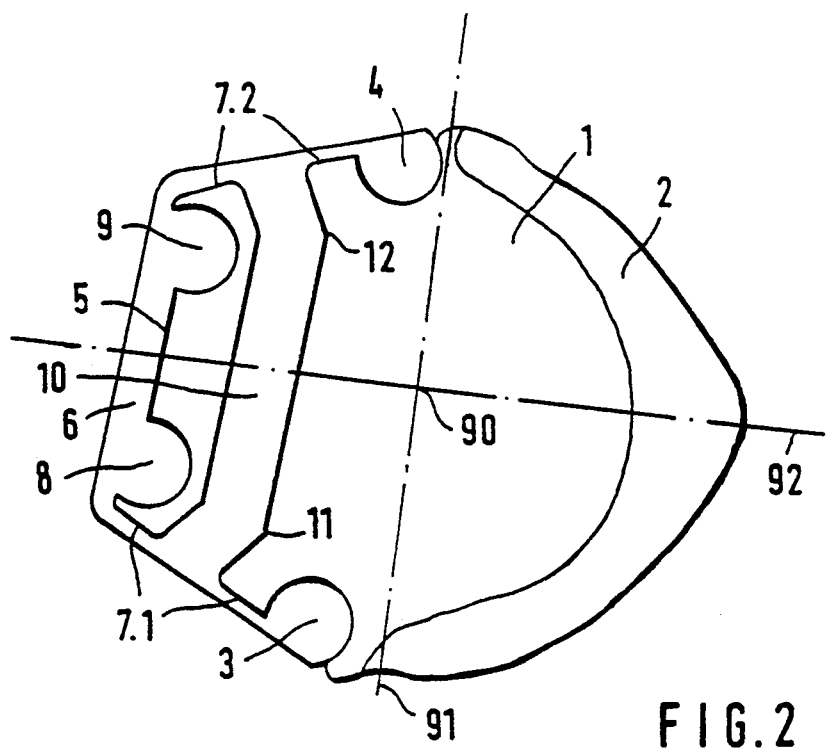
FIG. 2 is an occlusal view of another dental crown or matrix.

FIG. 2 is an occlusal view of another matrix in the form of a crown 1 with two supporting surfaces 7.1 and 7.2. A stump with a crown of this type can act as a post for a prosthesis which extends to each side. Friction is increased by two friction grooves 8 and 9 in the lingual functional surface 5 and by two angles 11 and 12 in channel 10.

Figure 3:
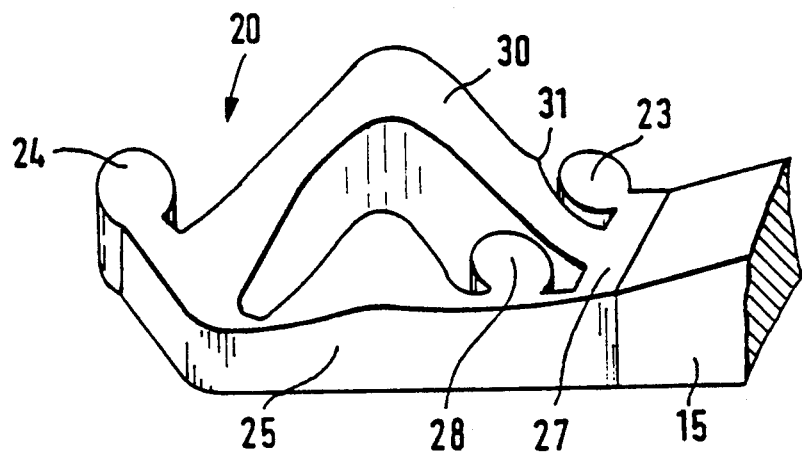
FIG. 3 is a perspective view of a patrix to match the matrix illustrated in FIG. 1 and which acts as a connector for a removable prosthesis.

FIG. 3 is a perspective view of a patrix 20 that matches the crown 1 illustrated in FIG. 1. The patrix is secured to a prosthesis saddle 15. The patrix includes friction cylinders 23, 24, and 28, a lingual outer telescope wall 25, a supporting telescope wall 27, and a patrix web 30 extending out of them and provided with an angle 31. These elements of the patrix are shaped correspondingly to above described grooves in the matrix so that the matrix and the patrix can interfit and frictionally engage. The upper surface of the patrix 20 and its hidden lower surface are adapted to the anatomy of the teeth being repaired.

Since the friction cylinders 23 and 24 are separate elements from the patrix web 30, it is possible to reactivate the patrix 20, as the friction abates, by bending the cylinders inward.

Experience demonstrates that the advantages of the patrix-and-matrix structure in accordance with the invention are most evident when the height of the cooperating telescoping surfaces of the two components is less than 3 mm. It is only at such low heights that the supragingival cervical offset 6 of FIGS. 1 and 2 must be included. The cervical offset may have a width of 0 mm when the patrix and matrix are approximately 3 mm high and of approximately 1 mm when they are 2 mm high.

Figure 4:
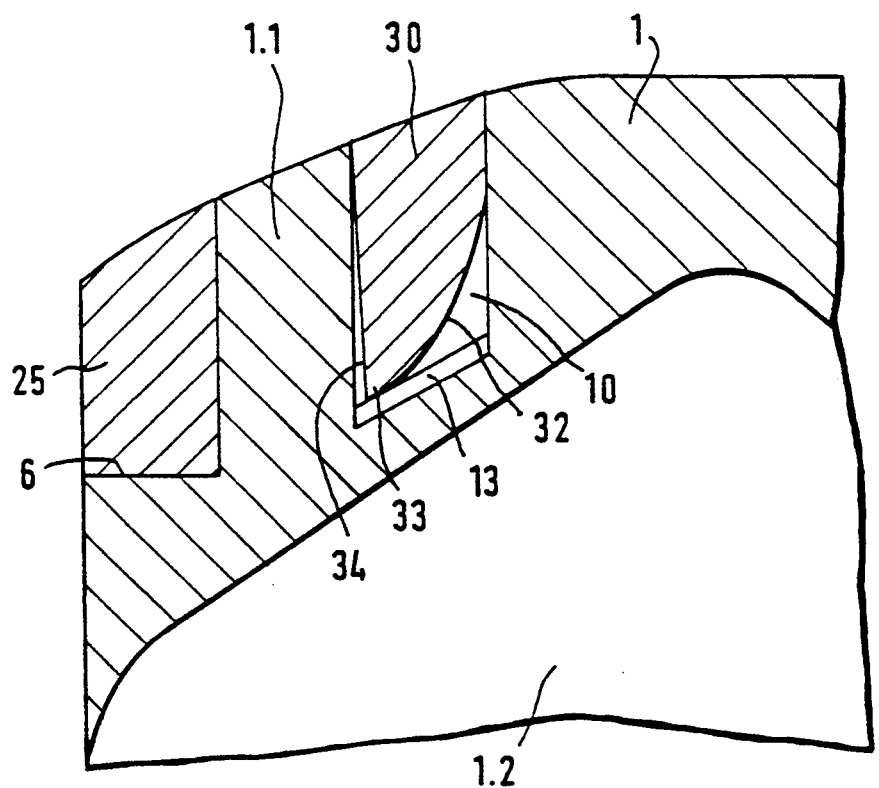
FIG. 4 is a detail of a transverse section through the matrix illustrated in FIG. 1 with the patrix illustrated in FIG. 3 fitting into it.

FIG. 4 is a cross-section, generally along the transverse midline 92, through the matrix 1, with the patrix 20 inserted in the vicinity of the outer telescope wall 25 and the patrix web 30. The outer telescope wall 25 and patrix web 30 surround the crown web 1.1 on all sides like a full telescoping connection. The bottom of the channel 10 slopes down toward the surface 5, adapting it to a stump of conventional shape, and derived from a stump cavity 1.2. Another function, however, is performed by the wedge shape of the lower surface 32 of the patrix web 30. The pressures that act on the prosthesis force it against the mucous membrane. The motion is transmitted to the patrix web 30, which is also forced down. The sharp edge 33 of the wedge slides toward the tongue, considerably increasing the surface-to-surface pressure between the patrix web 30 and the walls of channel 10. This is especially true when, as illustrated in FIG. 4, the lingual surface 34 of the patrix web 30 tapers slightly conically.

The surface-to-surface pressure is also improved and the rigid attachment between the matrix 1 and the patrix 20 is accordingly reinforced by the ridge 13 on the bottom of channel 10. This shifts the apparent fulcrum of the patrix 20 on the matrix 1 from the supragingival offset 6 in the vicinity of the supporting surface 7 to the ridge 13. This procedure increases the pressures that occur on the supporting surface 7 due to the process of mastication, increasing friction, instead of eliminating them.

The hold of the rigid attachment obtained with a telescoping connection depends strictly on the patrix 20 and the matrix 1 shifting and skewing as little as possible in relation to each other. This ensures enough friction to resist the forces exerted on the prosthesis and on the rigid connector during mastication.

Figure 5:
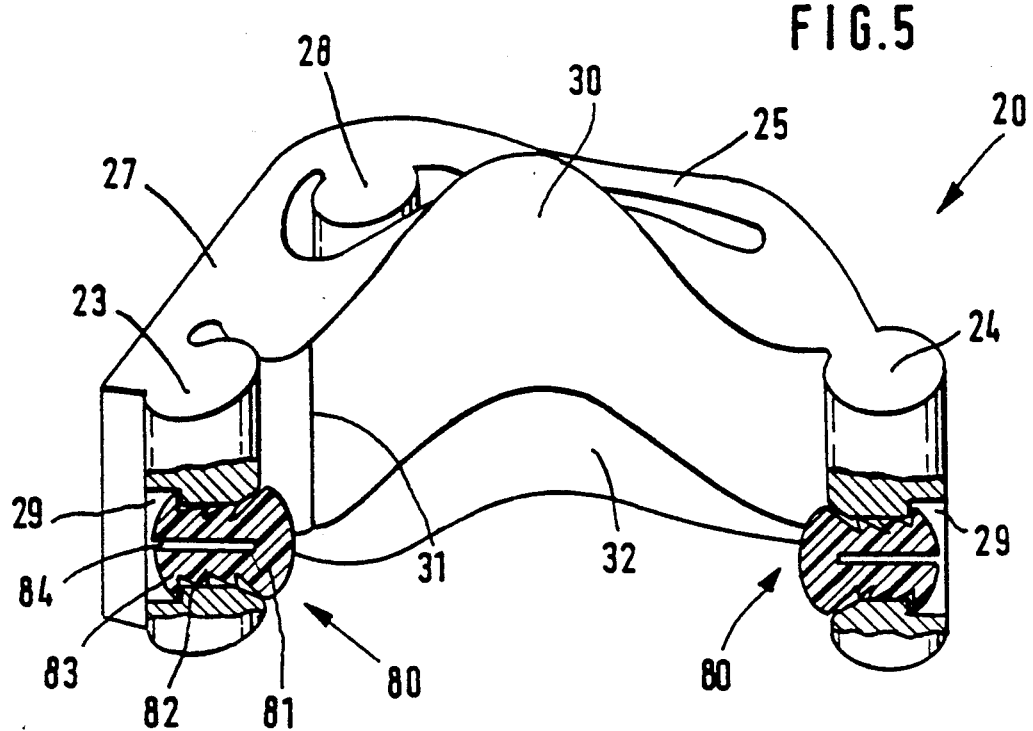
FIG. 5 is another perspective view of the patrix illustrated in FIG. 3 with additional replaceable friction elements.

FIG. 5 is a perspective view of the patrix 20 rotated 180° in relation to the view in FIG. 3. Each friction cylinder 23, 24, and 28 has a transverse bore 29, into which a friction element 80 is inserted from the front. The friction element is made of resilient plastic and has a convex head 81, with a free forward surface which acts as a friction surface. The convex rear surface of the head 81 extends into a conical countersink in the transverse bore 29. The convex head 81 accordingly functions simultaneously as a spring and as a friction element. The resulting structure takes up very little space.

Extending out of the rear of the head 81 is a shaft 82 which is surrounded by expansion skirts 83. An optional longitudinal slot 84 in the shaft 82 can be employed to control its elasticity. The expansion skirts 83 are intended only to secure the shaft 82 in the transverse bore 29.

Friction elements 80 eliminate any metal-to-metal friction while the prosthesis is being inserted and removed. The use of three friction elements 80 statically secures the patrix 20 in the crown 1. Friction forces can be intentionally controlled by varying the shape and size of the convex head 81. Friction elements 80 can easily be replaced when necessary.

Depressions can be introduced into the friction grooves 3, 4, and 8 in the matrix 1 at points which are opposite the convex heads 81 of friction elements 80 to secure the patrix 20 by interlocking it to the heads 81 as well as holding it by friction.

Details as to the shape and size of friction elements 80 are found in German Utility Model publication U 9 103 022.6, which represents priority.

Precision in the manufacture of the matrix and the patrix determines the unexceptionable function of the telescoping design according to the invention. Although such precision can be attained by prefabricating the elements of the telescope on an industrial scale, because the teeth being repaired can differ extensively, only individual finishing of each telescoping connection is possible at the present state of the art. In this context, with the present invention, it is also possible to use industrially prefabricated telescoping connections when the principles behind the present invention are consistently observed. For this purpose, the technician is supplied not only with an industrially prefabricated patrix but also with a ceramic core 50 that fits into the patrix precisely. This is used to simplify the manufacture of the matrix or crown 1. Ceramic cores in prosthetic teeth have been known up to now only in industrially prefabricated attachments, like T attachments, for example.

Figure 6:
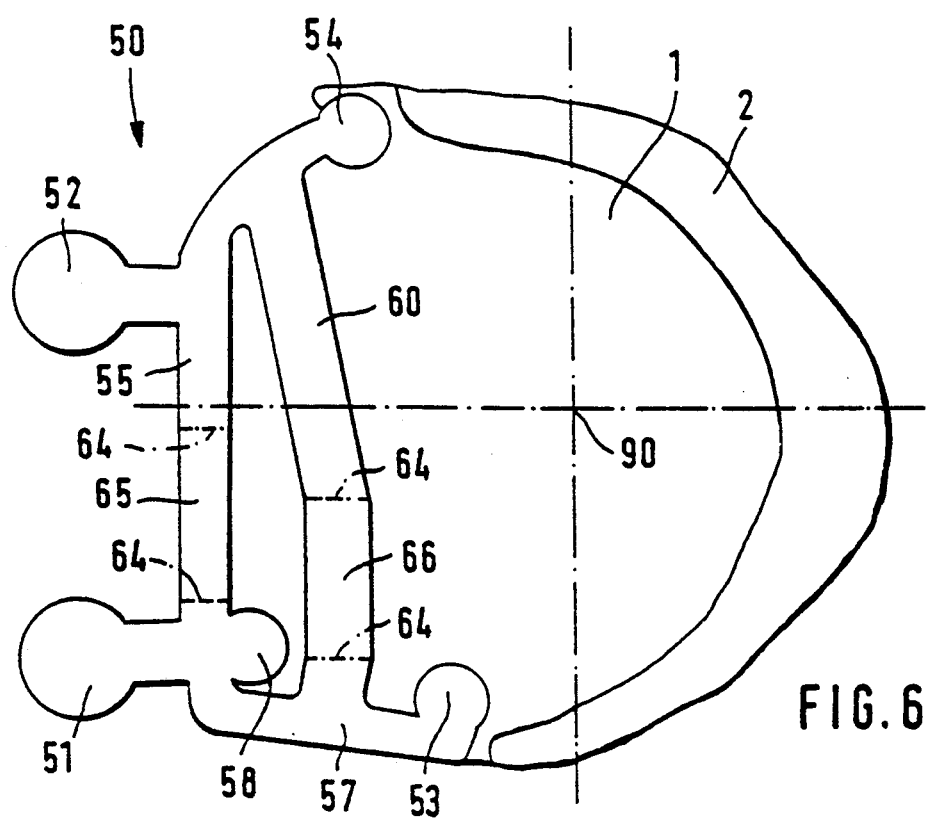
FIG. 6 is an occlusal view of the crown illustrated in FIG. 1 with a ceramic core inserted into it.

FIG. 6 is an occlusal view of a crown 1 with such a ceramic core 50 installed in the crown. The cross-section of the core essentially matches the empty spaces in the crown. Friction grooves 53, 54, and 58, a lingual outer core wall 55, a supporting core wall 57, and a core web 60 are apparent.

In the vicinity of the outer core wall 55 are two cylindrical holders 51 and 52. Their function is now described. The shape of the ceramic core 50 makes it possible to extrude it, which makes it considerably cheaper, even in relation to the ceramic cores used in T attachments in the art.

Since the teeth being repaired are different, the procedure will involve producing and keeping a large number of ceramic cores 50 of varying width. But this situation would basically be acceptable given the relatively low price. FIG. 6, however, illustrates another solution. It is possible to separate a wide ceramic core 50 along a line 64, remove the separate extenders 65 and 66, and combine the two halves of the core again with no gap between them.

Another possibility is to begin with a narrow width ceramic core 50 to them and insert extenders 65 and 66 which are made out of modeling compound, for example. It is, finally, even possible to model the two halves of the core directly onto the stump of the tooth and grind off the metal webs that occur during the later casting.

It will be obvious that the ceramic core 50 must be widened or narrowed with a conventional paralleler, which can readily be secured to the cylindrical holders 51 and 52. The paralleler will in any event also be employed to correctly position the ceramic core 50 on the tooth stump while the technician models the crown 1 in wax.

Figure 7:
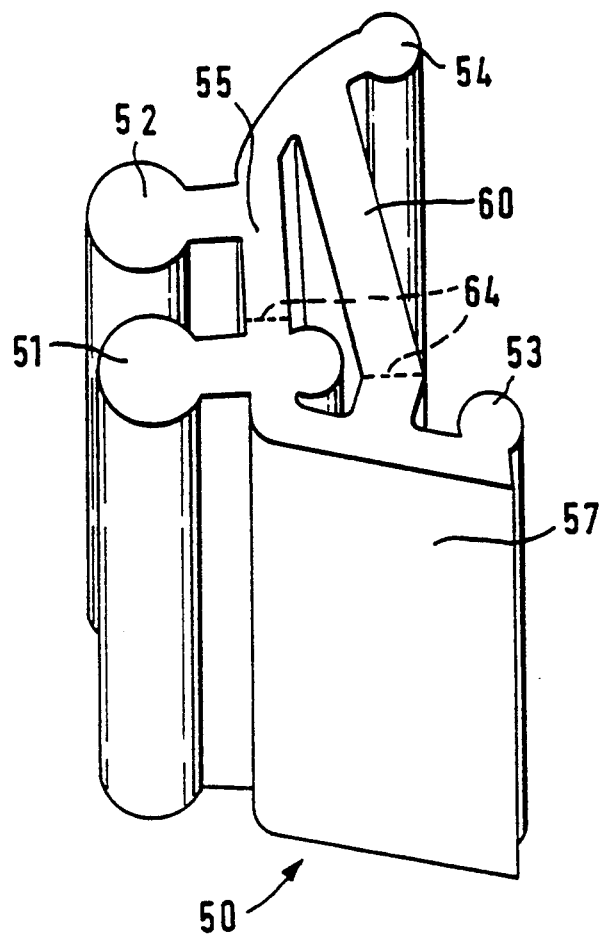
FIG. 7 is a perspective view of the ceramic core illustrated in FIG. 6 in the unfinished state.

FIG. 7 is a perspective view of a ceramic core 50 trimmed from an extruded billet. A supporting core wall 57 with a core cylinder 53 and core web 60 are toward the front, an outer core wall 55 with two integrated cylindrical holders 51 and 52 are to the left, and another core cylinder 54 is to the rear. Also illustrated are lines 64 of separation.

Figure 8:
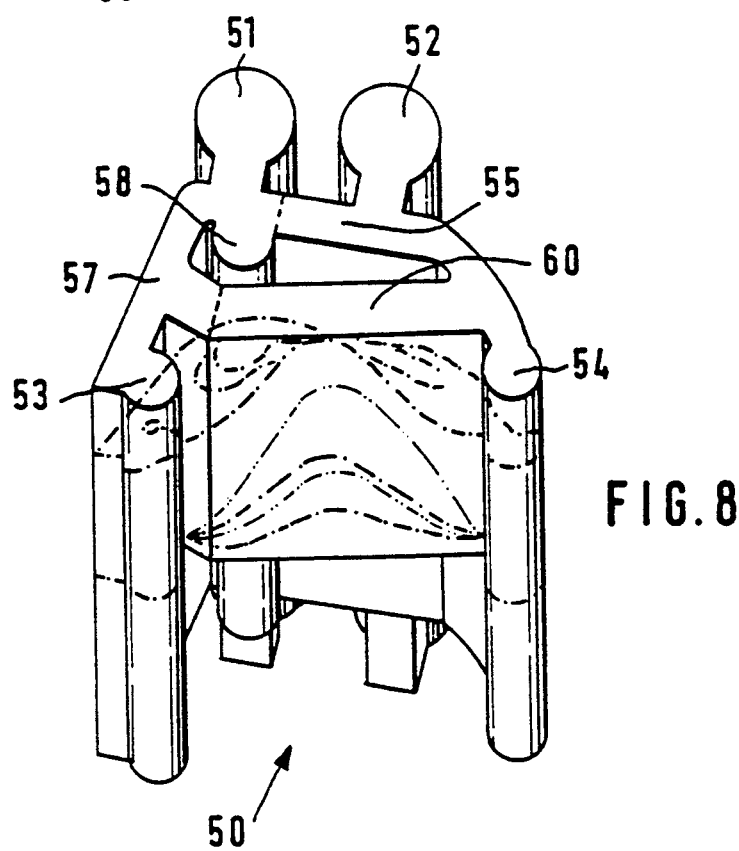
FIG. 8 is another perspective view of the ceramic core illustrated in FIG. 6.

FIG. 8 is another perspective view of the outer core wall 55. The final shape that the technician creates from the semifinished product is adapted to the anatomy of the teeth being repaired, and is represented by the dot-and-dash lines. Since, however, the factory prefabricated parallel surfaces are left as they are the metal cast crown 1 will have similar precisely parallel and dimensionally stable telescoping surfaces for the also industrially prefabricated patrix to fit unexceptionably against, as illustrated in FIG. 3.

Figure 9:
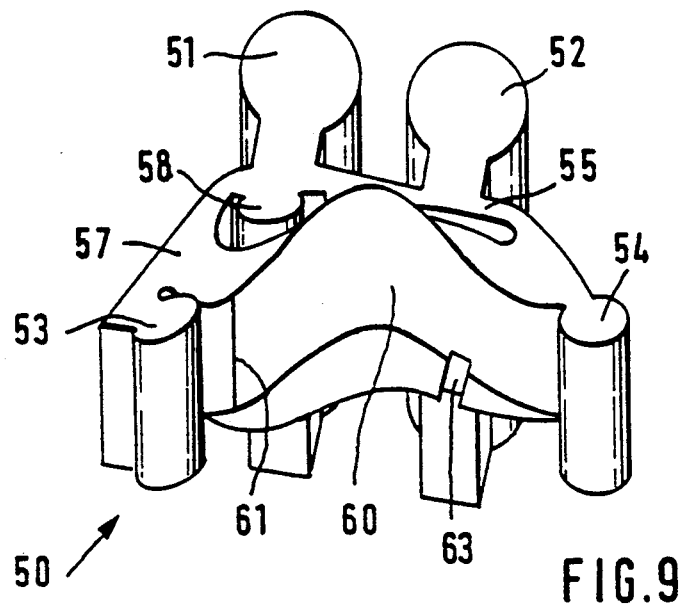
FIG. 9 is a perspective view of the ceramic core illustrated in FIGS. 6, 7, and 8 after it has been finished by the dental technician.

FIG. 9 illustrates the finished ceramic core 50. A negative offset 63 that corresponds to ridge is 13 introduced into the bottom surface of core web 60

Figure 10:
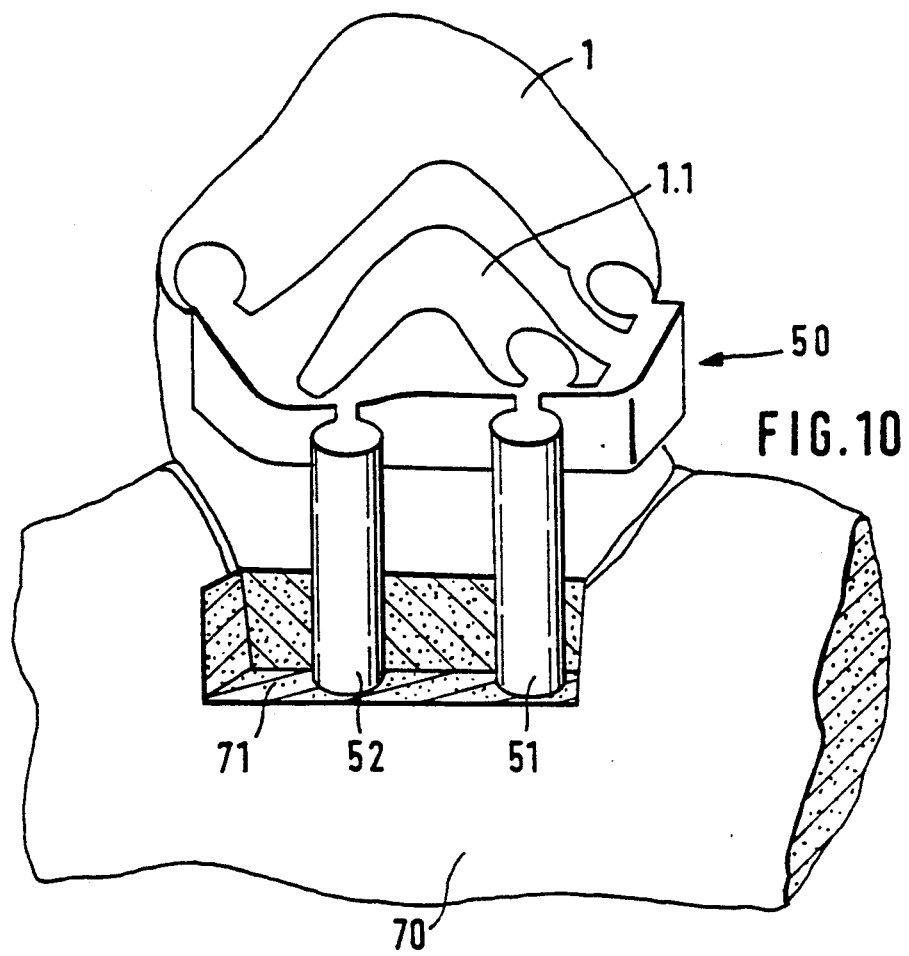
FIG. 10 is a perspective view of a dental crown cast in metal using the ceramic core illustrated in FIGS. 6 through 9 and resting on part of a model jaw.

FIG. 10, finally, illustrates a jaw casting 70 with a crown 1 resting on it. Crown 1 has a ceramic core 50. It is evident that cylindrical holders 51 and 52 project below the lower edge of the ceramic core 50. The technician has introduced a cutout 71 in the casting 70. Cylindrical holders 51 and 52 rest against the bottom of the cutout, considerably simplifying the modeling process. Since cylindrical holders 51 and 52 do not need to project upward, it is always possible to verify the precise shape of the crown 1 by resting the countervailing tooth against it.

The present invention will on the whole ensure a rigid connector for a removable dental prosthesis whereby industrial prefabrication of the components relevant to rigid connection will increase precision, reduce manual labor, improve function, extend life, augment reliability, and ensure uniform results even when the technician is not highly trained. The invention also makes it possible for the first time to obtain a rigid connection with an overall height of less than 3 mm.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A dental crown as a matrix for being telescopingly applied to and removably secured to a rigid connector as patrix, for providing a removable prosthetic tooth, the dental crown matrix comprising:
   a plurality of parallel walls adapted for telescopingly passing over and meeting with corresponding parallel walls on the connector;
   a first and a second friction grooves defined by respective ones of the walls;
   a lingual functional surface, generally extending between the first and second friction grooves; an outer surface on the opposite side from the lingual functional surface;
   a supergingival cervical offset in the vicinity of the lingual functional surface;
   the connector including a saddle by which the connector is secured in the mouth; the crown matrix including a supporting surface generally adjacent and facing toward the saddle; the first friction groove being defined in and along the supporting surface; the second friction groove being away from the surface of which the first friction groove is formed; a third friction groove in the lingual functional surface;
   an intracoronal channel extending across the crown, generally parallel to the lingual functional surface and displaced from both of the first and the second friction grooves toward the lingual functional surface;
   all of the grooves, the channel and the cervical offset being defined by the parallel walls.

2. The dental crown of claim 1, wherein the supporting surface facing toward the saddle is generally flat, except for the first friction groove defined therein.

3. The dental crown of claim 1, wherein the supragingival offset extends along the crown generally into the vicinity of the supporting surface.

4. The dental crown of claim 1, wherein the height of the functional surfaces and grooves of the patrix and matrix are related to the width of the supragingival offset, such that the shorter are the surfaces and grooves of the patrix and matrix, the wider is the supragingival offset, such that when those surfaces are of a certain height, the supragingival offset is of no width.

5. The dental crown of claim 1, wherein the supporting surface is oriented at an angle in the range of 20° to 90° with respect to the midline of the jaw or maxillary crest of the person receiving the crown.

6. The dental crown of claim 1, further comprising a second supporting surface on the side which is opposite the first mentioned supporting surface and facing generally away from the first supporting surface.

7. The dental crown of claim 6, wherein the intracoronal channel extends between and into each of the first and of the second supporting surfaces.

8. The dental crown of claim 1, further comprising a fourth of the friction groove, also defined in the lingual functional surface and spaced from the third friction groove.

9. The dental crown of claim 1, further comprising a snap in groove in the supporting surface for receiving an active fastener.

10. The dental crown of claim 1, wherein the lingual functional surface is essentially flat.

11. The dental crown of claim 1, wherein the intracoronal channel extends across the tooth and has at least one angle bend along its length.

12. The dental crown of claim 1, wherein the intracoronal channel extends into and intersects the supporting surface.

13. The dental crown of claim 1, further comprising a ridge defined on the bottom of the intracoronal channel.

14. The dental crown of claim 13, wherein the ridge is disposed along the channel on the other side of the transverse midline of the dental crown from the supporting surface.

15. The dental crown of claim 1, wherein the intracoronal channel has a bottom which slopes across the channel toward one of the lingual functional surface and the outer surface of the dental crown.

16. The dental crown of claim 1, wherein the intracoronal channel has sidewalls and other functional surfaces defined in one of the channel walls.

17. The dental crown of claim 16, wherein the other functional surface in the one channel wall further comprises a fourth friction groove defined in the one channel wall.

18. In combination, the dental crown of claim 1 and the releasable rigid connector for the dental crown, the connector comprising:
   a supporting telescope wall including a surface for cooperating with the supporting surface of the crown and which is parallel thereto, the connector including a saddle for attachment of the connector in a jaw, and the supporting telescope wall being adjacent the saddle;
   a first friction cylinder attached to the telescope wall and having walls which are parallel to the walls of the first friction groove, so that the first friction cylinder is frictionally received in the first friction groove of the crown;
   a lingual outer telescope wall which is shaped and positioned parallel to and for being received in the supragingival cervical offset of the crown;
   a patrix web extending across the connector from the supporting telescope wall as far as an outer telescope wall which is spaced away from the supporting telescope wall;

a second friction cylinder spaced away from the first friction cylinder and placed and shaped for being received in the second groove of the crown;

a third friction cylinder supported on the connector, shaped and placed for being received in the third friction groove of the crown;

the patrix web being shaped to fit into the intracoronal channel of the crown.

19. The combination of claim 18, wherein the patrix web is wedge shaped, the wedge shape including a sharp edge extending into the channel and facing toward one of the lingual or opposite sides of the channel.

20. The combination of claim 18, and further comprising a core, the core having a cross-section which is complementary to the cross section of the crown, and the core having projecting elements corresponding to the grooves and the channels in the crown.

21. A releasable rigid connector for having secured to it a removable tooth prosthesis crown, the connector comprising:

a supporting telescope wall including a surface for cooperating with a supporting surface of the crown and which is parallel thereto, the connector including a saddle for attachment of the connector in a jaw, and the supporting telescope wall being adjacent the saddle;

a first friction cylinder attached to the telescope wall and having walls which are parallel to the walls of a first friction groove in the crown, so that the first friction cylinder may be frictionally received in the first friction groove of the crown;

a lingual outer telescope wall which is shaped and positioned parallel to and for being received in a supragingival cervical offset of the crown;

a patrix web extending across the connector from the supporting telescope wall and toward the opposite side of the connector, at which there is an outer telescope wall which is spaced away from the supporting telescope wall;

a second friction cylinder spaced away from the first friction cylinder and placed and shaped for being received in a second groove of the crown;

a third friction cylinder supported on the connector and placed and shaped for being received in a third friction groove of the crown;

the patrix web being shaped to fit into an intracoronal channel of the crown.

22. The connector of claim 21, wherein the patrix web is wedge shaped, the wedge shape including a sharp edge for extending into the channel of the crown and facing toward one of the lingual or opposite sides of the channel.

23. The releasable connector of claim 21, wherein the patrix web has a side facing the other of the lingual or the opposite sides from the sharp edge and the other web side is slightly conical in shape.

24. The connector of claim 23, wherein a transverse bore is defined in at least one of the friction cylinders;

a friction element inserted into the transverse bore and projecting out of the transverse bore for enhancing frictional engagement with respective surfaces of the crown.

25. The connector of claim 24, wherein the friction element in the bore has a convex head and a friction surface defined on the front of the head, the friction element having a shaft in the bore; expansion skirts around the shaft.

26. The connector of claim 25, wherein the friction element has a longitudinal slot therealong and is made of a resilient plastic material.

* * * * *